United States Patent [19]

Shenoy

[11] 4,065,474
[45] Dec. 27, 1977

[54] 1,4-BENZODIAZEPINE-2-AMINE DERIVATIVES

[75] Inventor: Umakant Devdas Shenoy, London, England

[73] Assignee: DDSA Pharmaceuticals Limited, Leicester, England

[21] Appl. No.: 689,303

[22] Filed: May 24, 1976

[30] Foreign Application Priority Data

May 22, 1975 United Kingdom ............... 22057/75

[51] Int. Cl.² .......................................... C07D 405/12
[52] U.S. Cl. ............................. 260/347.7; 260/296 B; 260/347.2
[58] Field of Search ............... 260/347.7, 296 B, 347.2

[56] References Cited

PUBLICATIONS

V. Braun et al., Ch. Abstr., (1931) vol. 25, pp. 1812–1814.

Primary Examiner—Henry R. Jiles
Assistant Examiner—Bernard Dentz
Attorney, Agent, or Firm—Burgess, Dinklage & Sprung

[57] ABSTRACT

Benzodiazepine derivatives having the general formula I:

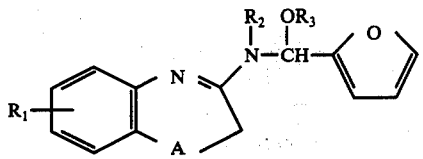

wherein
$R_1$ represents a hydrogen or halogen atom or a trifluoromethyl, cyano, nitro, lower alkyl, lower alkoxy or lower alkyl thio group;
$R_2$ represents a lower alkyl, hydroxy-(lower alkyl), lower alkenyl or benzyl group;
$R_3$ represents a lower alkyl or substituted lower alkyl group; and
—A— represents a grouping of the general formula:

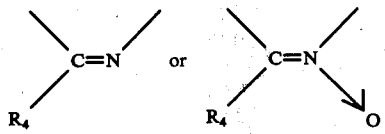

in which $R_4$ represents a phenyl, (lower alkyl)-phenyl, nitrophenyl, halophenyl or pyridyl group which have sedation and hypnotic activity and a method for their preparation.

6 Claims, No Drawings

1,4-BENZODIAZEPINE-2-AMINE DERIVATIVES

The invention relates to novel benzodiazepine derivatives and their acid addition salts, to a method for their preparation and to pharmaceutical compositions containing them.

The novel benzodiazepine derivatives according to this invention have the general formula I:

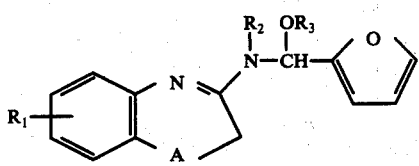

in which the symbols are as defined below. The invention also provides acid additions salts of the above compounds I, preferably with therapeutically acceptable inorganic or organic acids such as hydrochloric acid, hydrobromic acid, nitric acid, sulphuric acid, acetic acid, formic acid, phosphoric acid, perchloric acid, succinic acid, maleic acid, citric acid and fumaric acid.

In the above formula I:

$R_1$ represents a hydrogen or halogen atom or a trifluoromethyl, cyano, nitro, lower alkyl, lower alkoxy or lower alkyl thio group;

$R_2$ represents a lower alkyl, hydroxy-(lower alkyl), lower alkenyl or benzyl group;

$R_3$ represents a lower alkyl or substituted lower alkyl group; and

—A— represents a grouping of the general formula:

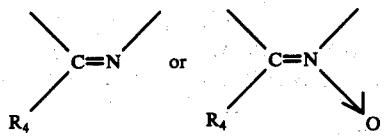

in which $R_4$ represents a phenyl, (lower alkyl)-phenyl, nitrophenyl, halophenyl or pyridyl group.

As used herein, the term "halogen" means fluorine, chlorine, bromine or iodine. The term "lower alkyl" refers to both straight-chain and branched-chain alkyl groups containing from 1 to 10 carbon atoms, for example methyl, ethyl, n-propyl, isopropyl, n-butyl, n-amyl and n-hexyl. The term "lower alkoxy" refers to both straight-chain and branched-chain alkoxy groups containing from 1 to 6 carbon atoms, for example methoxy, ethoxy and n-butoxy.

The term "lower alkenyl" refers to both straight-chain and branched-chain alkenyl groups containing from 2 to 6 carbon atoms, for example vinyl, allyl, n-butenyl, n-hexenyl and isobutenyl.

The new benzodiazepine compounds of the invention and their acid addition salts with therapeutically acceptable acids show the activity on the central nervous system typical of compounds with the benzodiazepine structure. They have been found to have sedation and hypnotic activities together with low toxicities which makes them potentially useful medicines. This invention accordingly provides pharmaceutical compositions comprising one or more such compounds in admixture with therapeutically acceptable diluents or carriers.

Specifically the compounds of the present invention are useful for their psychotropic action on the central nervous system, for their tranquillizing, sedative and hypnotic properties. In such treatment they are generally, employed in a dosage between 1 mg and 10 mg depending on the age and condition of the patient. In larger doses they produce sedation, and when the sedative dose is increased they have hypnotic effect. They can be applied in the form of a tablet, capsules, suppositories or syrup, or in injectable form. They can be formulated with adjuvants and excipients as is usual with products of this nature. This invention accordingly provides therapeutic compositions comprising one or more compounds according to this invention in admixture with a pharmacologically acceptable diluent or carrier.

The benzodiazepine compounds I can be prepared according to this invention from a 3H-1,4-benzodiazepine compound of the general formula II:

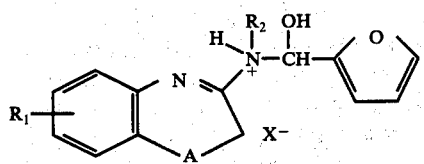

in which $R_1$, $R_2$ and —A— are as described above and $X^{31}$ represents an acid radical. This starting material is described and claimed in our British Patent Specification No. 1,359,287, the disclosure of which is hereby incorporated herein by reference, and may be prepared by treating an aqueous or aqueous/alcoholic solution of a 3H-1,4-benzodiazepine compound of the general formula III:

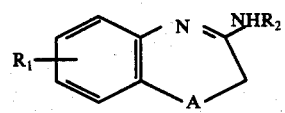

in which $R_1$, $R_2$ and —A— are as above defined, or of an acid addition salt thereof, with a molar equivalent or excess of furfuraldehyde, preferably with from 1 to 6 moles of furfuraldehyde per mole of the compound III in acid conditions. The reaction is preferably carried out at from 0° C to 20° C and generally takes up to 60 hours. The acid conditions are preferably provided by up to 4 moles of acid, for example hydrochloric or sulphuric acid, per mole of the compound III (basic form). Preferably 1 mole of the compound III is reacted with 2 moles of furfuraldehyde in the presence of 2 moles of acid.

The compounds II may be converted to the corresponding compounds I by a process according to this invention which comprises treating a solution of the appropriate compound II in an alcohol $R_3OH$ with an excess of an aqueous alkali. Suitable alkalis include aqueous potassium and sodium hydroxides in concentrations of 5% to 40% w/v. The product I should be precipitated after a short period, for example 1 hour or less, by dilution of the reaction mixture with water.

The following Example illustrates the invention.

EXAMPLE

Furfuraldehyde (12 ml) was added to a stirred solution of 7-chloro-2-methylamino-5-phenyl-3H-1,4-benzodiazepine-4-oxide hydrochloride (chlordiazepoxide hydrochloride) (33.6 g) in water (400 ml) and concentrated hydrochloric acid (15 ml) and the reaction mixture was stirred for 60 hours. The resulting precipitate was filtered, washed with water (2 portions of 25 ml each) and air dried. Crystallization at room temperature from a mixture of methanol, diethyl ether and petroleum ether gave 6 g of off-white crystals of 7-chloro-2-(N-methyl-N-1-hydroxyfurfurylamino)-5-phenyl-3H-1,4-benzodiazepine-4-oxide hydrochloride, melting at 148° to 150° C with decomposition.

Analysis of the product gave the following results:

Calculated for $C_{21}H_{19}Cl_2N_3O_3$: C= 58.3%, H=4.4%; N=9.7%. Found: C= 58.4%,H=4.3%,N=9.7%.

40% w/v aqueous sodium hydroxide (2 ml) was added to a solution of the above product (3.3 g) in methanol (30 ml) and the reaction mixture was stirred for 30 minutes. At the end of that time the reaction mixture was diluted with water to precipitate the reaction product. This was filtered, washed with water until free from alkali and air dried. Crystallization at room temperature from a mixture of methanol, diethyl ether and petroleum ether gave 300 mg. of creamy crystals of 7-chloro-2-(N-methyl-N-1-methoxyfurfurylamino)-5-phenyl-3H-1,4-benzodiazepine-4-oxide, melting at 141° to 142° C.

Analysis of the product gave the following results:

Calculated for $C_{22}H_{20}ClN_3O_3$: C= 64.5%,H=4.9%,N=10.3%. Found: C= 64.0%,H=5.1%,N=10.2%.

What we claim is:

1. A benzodiazepine derivative of the formula I

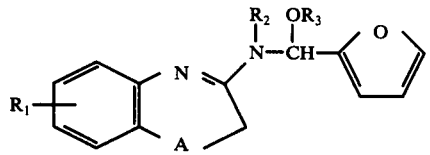

in which $R_1$ represents a hydrogen or halogen atom or trifluoromethyl, cyano, nitro, lower alkyl, lower alkoxy or lower alkyl thio;

$R_2$ represents lower alkyl, hydroxy-(lower alkyl), lower alkenyl or benzyl;

$R_3$ represents lower alkyl; and

—A— represents a grouping of the formula:

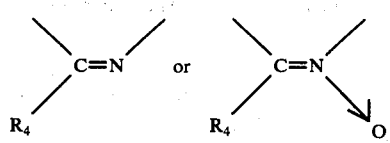

in which $R_4$ represents phenyl, (lower alkyl)-phenyl, nitrophenyl, halophenyl or pyridyl.

2. 7-chloro-2-5-phenyl-3H-1,4-benzodiazepine-4-oxide.

3. A therapeutically acceptable acid addition salt of benzodiazepine derivative according to claim 1.

4. An acid addition salt according to claim 3, in which the acid is hydrochloric acid, hydrobromic acid, nitric acid, sulphuric acid, acetic acid, formic acid, phosphoric acid, perchloric acid, succinic acid, maleic acid, citric acid and fumaric acid.

5. A process for preparing a benzodiazepine derivative according to claim 1, which comprises treating a solution of the corresponding compound II

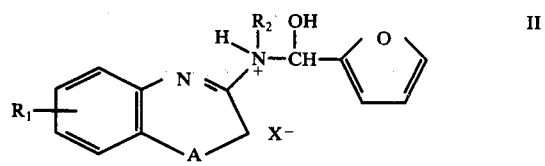

in which $R_1$, $R_2$ and —A— are as described above and $X^-$ represents an acid radical, in an alcohol $R_3OH$ in which $R_3$ represents lower alkyl with an excess of an aqueous alkali.

6. A process according to claim 5 wherein the aqueous alkali is potassium or sodium hydroxide at a concentration of 5% to 40% w/v.

* * * * *

UNITED STATES PATENT AND TRADEMARK OFFICE
CERTIFICATE OF CORRECTION

PATENT NO. : 4,065,474
DATED : December 27, 1977
INVENTOR(S) : Umakant Devdas Shenoy It is certified that error appears in the above-identified patent and that said Letters Patent are hereby corrected as shown below:

Column 2, line 28, "$X^{31}$" should read -- $X^-$ --.

Signed and Sealed this

Eleventh Day of July 1978

[SEAL]

Attest:

RUTH C. MASON
*Attesting Officer*

DONALD W. BANNER
*Commissioner of Patents and Trademarks*